(12) United States Patent
Yoshida et al.

(10) Patent No.: US 11,013,110 B2
(45) Date of Patent: May 18, 2021

(54) RECEIVER AND RECEIVING SYSTEM

(71) Applicant: NIPPON MEKTRON, LTD., Tokyo (JP)

(72) Inventors: Akio Yoshida, Tokyo (JP); Mitsunori Sasaki, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 284 days.

(21) Appl. No.: 16/103,594

(22) Filed: Aug. 14, 2018

(65) Prior Publication Data

US 2019/0069399 A1 Feb. 28, 2019

(30) Foreign Application Priority Data

Aug. 31, 2017 (JP) .............................. JP2017-167032

(51) Int. Cl.
| | | |
|---|---|---|
| A61B 5/00 | (2006.01) | |
| H05K 1/02 | (2006.01) | |
| H04B 13/00 | (2006.01) | |
| G01S 5/06 | (2006.01) | |
| H01Q 7/00 | (2006.01) | |
| H05K 1/16 | (2006.01) | |
| H01Q 1/27 | (2006.01) | |
| H01Q 1/40 | (2006.01) | |
| H01Q 21/29 | (2006.01) | |
| G01S 5/14 | (2006.01) | |
| A61B 5/06 | (2006.01) | |
| H01Q 1/38 | (2006.01) | |

(52) U.S. Cl.
CPC .......... *H05K 1/0283* (2013.01); *A61B 5/0015* (2013.01); *A61B 5/0024* (2013.01); *A61B 5/0028* (2013.01); *A61B 5/0031* (2013.01); *A61B 5/061* (2013.01); *G01S 5/06* (2013.01); *G01S 5/14* (2013.01); *H01Q 1/273* (2013.01); *H01Q 1/40* (2013.01); *H01Q 7/00* (2013.01); *H01Q 21/29* (2013.01); *H04B 13/005* (2013.01); *H05K 1/165* (2013.01); *A61B 2562/046* (2013.01); *A61B 2562/164* (2013.01); *H01Q 1/38* (2013.01); *H05K 2201/10098* (2013.01)

(58) Field of Classification Search
CPC ..... A61B 5/015; A61B 5/0024; A61B 5/0028; A61B 5/0031; A61B 5/0002; H05K 1/0283
USPC .................................................. 128/897, 899
See application file for complete search history.

(56) References Cited

U.S. PATENT DOCUMENTS

2009/0118576 A1 5/2009 Akagi et al.
2010/0002402 A1* 1/2010 Rogers ................ H01L 21/4867
361/749

(Continued)

FOREIGN PATENT DOCUMENTS

JP 2006-223567 A 8/2006
WO 2002/054932 A2 7/2002

(Continued)

*Primary Examiner* — John P Lacyk
(74) *Attorney, Agent, or Firm* — Studebaker & Brackett PC

(57) ABSTRACT

A receiver includes a stretchable circuit board having stretchability and a first antenna formed on a main surface of the stretchable circuit board, the first antenna being configured to stretch in accordance with the stretchable circuit board and configured to receive a signal transmitted from a transmitter installed in a living body.

17 Claims, 10 Drawing Sheets

(56) References Cited

U.S. PATENT DOCUMENTS

| | | | |
|---|---|---|---|
| 2010/0330338 A1* | 12/2010 | Boyce | B29C 59/02 |
| | | | 428/156 |
| 2011/0285835 A1 | 11/2011 | Koide | |
| 2014/0118201 A1* | 5/2014 | Im | H01Q 1/2225 |
| | | | 343/718 |
| 2016/0015962 A1* | 1/2016 | Shokoueinejad Maragheh | |
| | | | A61N 5/0616 |
| | | | 607/50 |
| 2016/0253892 A1* | 9/2016 | Hyde | G08B 21/0453 |
| | | | 340/686.1 |

FOREIGN PATENT DOCUMENTS

| | | |
|---|---|---|
| WO | 2010/068818 A2 | 6/2010 |
| WO | 2011/024560 A1 | 3/2011 |

\* cited by examiner

RECEIVER AND RECEIVING SYSTEM

CROSS-REFERENCE TO RELATED APPLICATION

This application claims priority from Japanese Patent Application No. 2017-167032 filed with the Japan Patent Office on Aug. 31, 2017, the entire content of which is hereby incorporated by reference.

BACKGROUND

1. Technical Field

The present disclosure relates to a receiver and a receiving system.

2. Description of the Related Art

Currently, a system configured to collect information in a living body to transmit, as data, the information to the outside of the body has been in practical use. Such information is collected by capturing an image in the living body, for example. In such a system, a sensor and a transmitter are installed in the body, for example, by swallowing. The sensor is configured to acquire the information in the living body. The transmitter has the function of transmitting the information acquired by the sensor to the outside of the body. Moreover, a receiver configured to receive the information transmitted by the transmitter is arranged in the vicinity of a body surface.

This system is, for example, described in WO 02002/054932 A, WO 02011/024560 A, JP-A-2006-223567, and WO 02010/068818 A.

According to a technique described in WO 02002/054932 A of the above-described patent literatures, a swallowable capsule having a transmission device and a video camera is installed in a human body, and an image signal transmitted from the capsule is received outside of the body. According to a technique described in WO 02011/024560 A, a capsule endoscope having a transmission function is installed in a living body. A receiving system described in WO 02011/024560 A has a receiving device and wireless relay devices. The receiving device is configured to receive a signal transmitted by the capsule endoscope. Each wireless relay device is configured to relay the signal between the capsule endoscope and the receiving device. According to the technique described in WO 02011/024560 A, the wireless relay devices are dispersively arranged at a jacket worn by a subject. Moreover, according to the technique described in WO 02011/024560 A, each wireless relay device is configured using a flexible substrate.

JP-A-2006-223567 describes a technique of a capsule endoscope medical examination system. The system described in JP-A-2006-223567 has a sensing device configured to sense a signal transmitted from an endoscope. The sensing device senses, as an electric displacement amount, the signal received by each of multiple loop antennas directly attached to a living body.

Moreover, according to a technique described in WO 02010/068818 A, an identifier device installed in a digestive system of a living body and a receiver fixed at an optional position of the living body are used to determine a digestive tract function.

The intensity of, e.g., the image signal transmitted from the capsule described in WO 02002/054932 A is weak. Thus, a receiver is preferably provided close to the living body. For this reason, according to the receiving system described in WO 02011/024560 A, the wireless relay devices are attached to the jacket, and therefore, are arranged in the vicinity of the subject's body. In the capsule endoscope medical examination system described in JP-A-2006-223567, the loop antennas are directly attached to the subject's body, and therefore, are arranged much closer to the subject's body.

SUMMARY

A receiver includes a stretchable circuit board having stretchability and a first antenna formed on a main surface of the stretchable circuit board, the first antenna being configured to stretch in accordance with the stretchable circuit board and configured to receive a signal transmitted from a transmitter installed in a living body.

DESCRIPTION OF THE EMBODIMENTS

Figure 1:
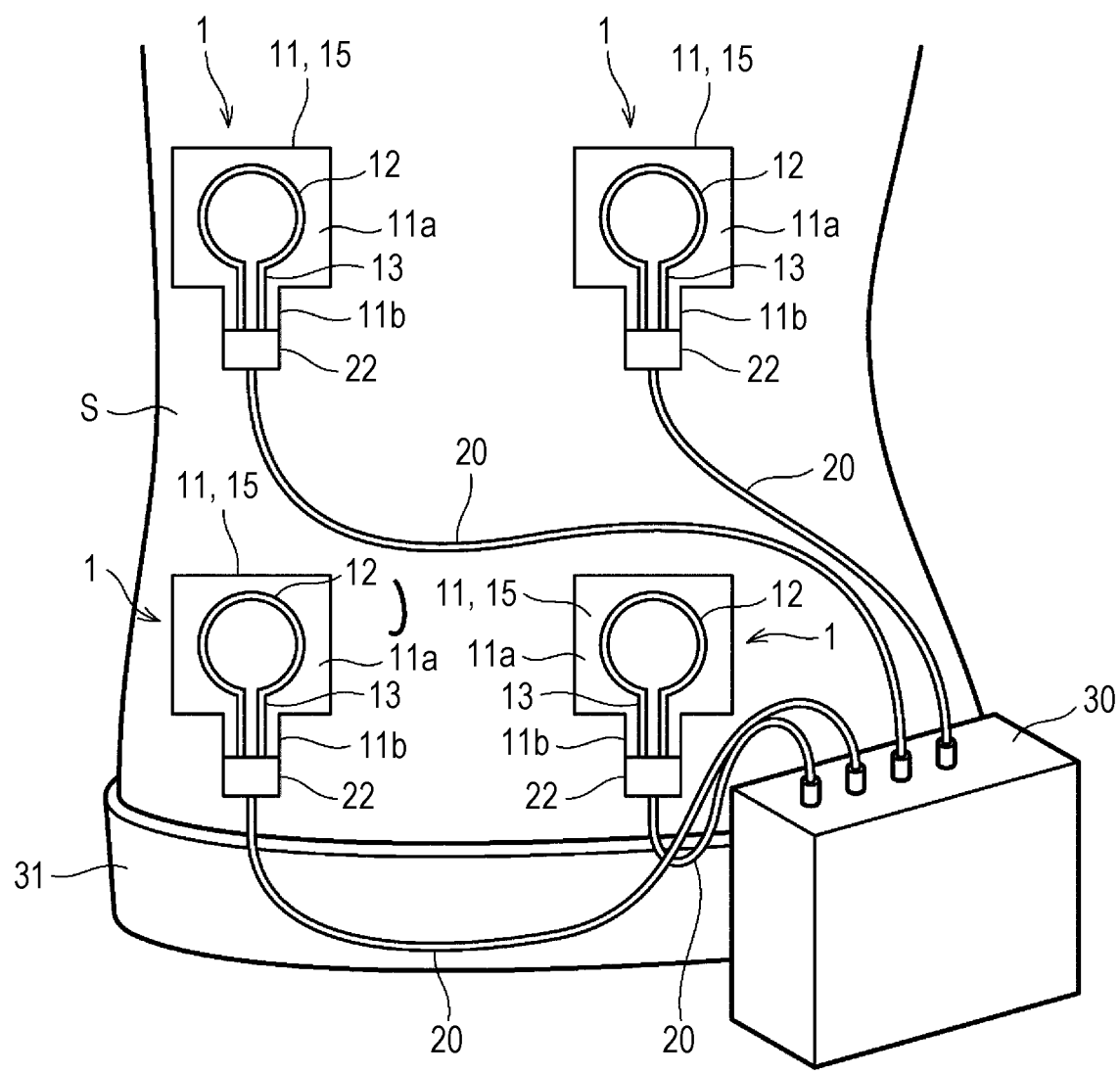
FIG. 1 is a view of a state when receivers according to a first embodiment of the present disclosure are attached to a subject's body.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In a case where the receivers such as the loop antennas are directly attached to the living body as in JP-A-2006-223567, receiving state of a loop antenna might change due to bending of the loop antenna when the subject moves body thereof, or the attached loop antennas might be detached because the loop antennas cannot follow motion of the body. For this reason, the receiving system described in JP-A-

2006-223567 has a problem that the movement of the subject during treatment is limited. According to the technique described in WO 02010/068818 A, the dimensions and shape of the receiver are downsized for reducing an uncomfortable feeling relating to the movement of the subject. However, limitations of the dimensions and shape of the receiver influences an effective length of the loop antenna. For this reason, the limitations of the dimensions and shape of the receiver are not preferred.

The present disclosure has been made in view of the above-described problems. The present disclosure relates to a receiver and a receiving system using the receiver. According to the receiver and the receiving system using the receiver, a load on a subject receiving treatment can be reduced, and high receiving sensitivity can be obtained.

A receiver according to one aspect of the present disclosure includes a stretchable circuit board having stretchability and a first antenna formed on a main surface of the stretchable circuit board, the first antenna being configured to stretch in accordance with the stretchable circuit board and configured to receive a signal transmitted from a transmitter installed in a living body.

The receiver according to one aspect of the present disclosure ay further include a second antenna configured to transfer the signal received by the first antenna.

The first antenna and the second antenna may be arranged in a two-sided relationship.

The first antenna may include multiple first antennas formed on the single stretchable circuit board.

The multiple first antennas may be arranged in a regular manner.

A receiving system according to an aspect of the present disclosure includes the receiver and a transmitter position detector configured to detect, based on a position and a received signal of each of the multiple first antennas of the receiver, a position of the transmitter in the living body, the transmitter having transmitted the signal received by the receiver.

According to the present disclosure, the receiver and the receiving system using the receiver can be provided, which are configured so that the load on the subject receiving the treatment can be reduced and high receiving sensitivity can be obtained.

Hereinafter, a first embodiment, a second embodiment, and a third embodiment of the present disclosure will be described. In the drawings according to the first to third embodiments, the same reference numerals are used to represent equivalent members, and part of description thereof will not be made. Moreover, the drawings according to the first to third embodiments mainly illustrate a relationship, arrangement, and the like for each configuration illustrated in the drawings. Thus, the drawings do not necessarily illustrate precise dimensions and shapes of the configurations, such as a length, a breadth, a width, and a height.

First Embodiment

Figure 2A:
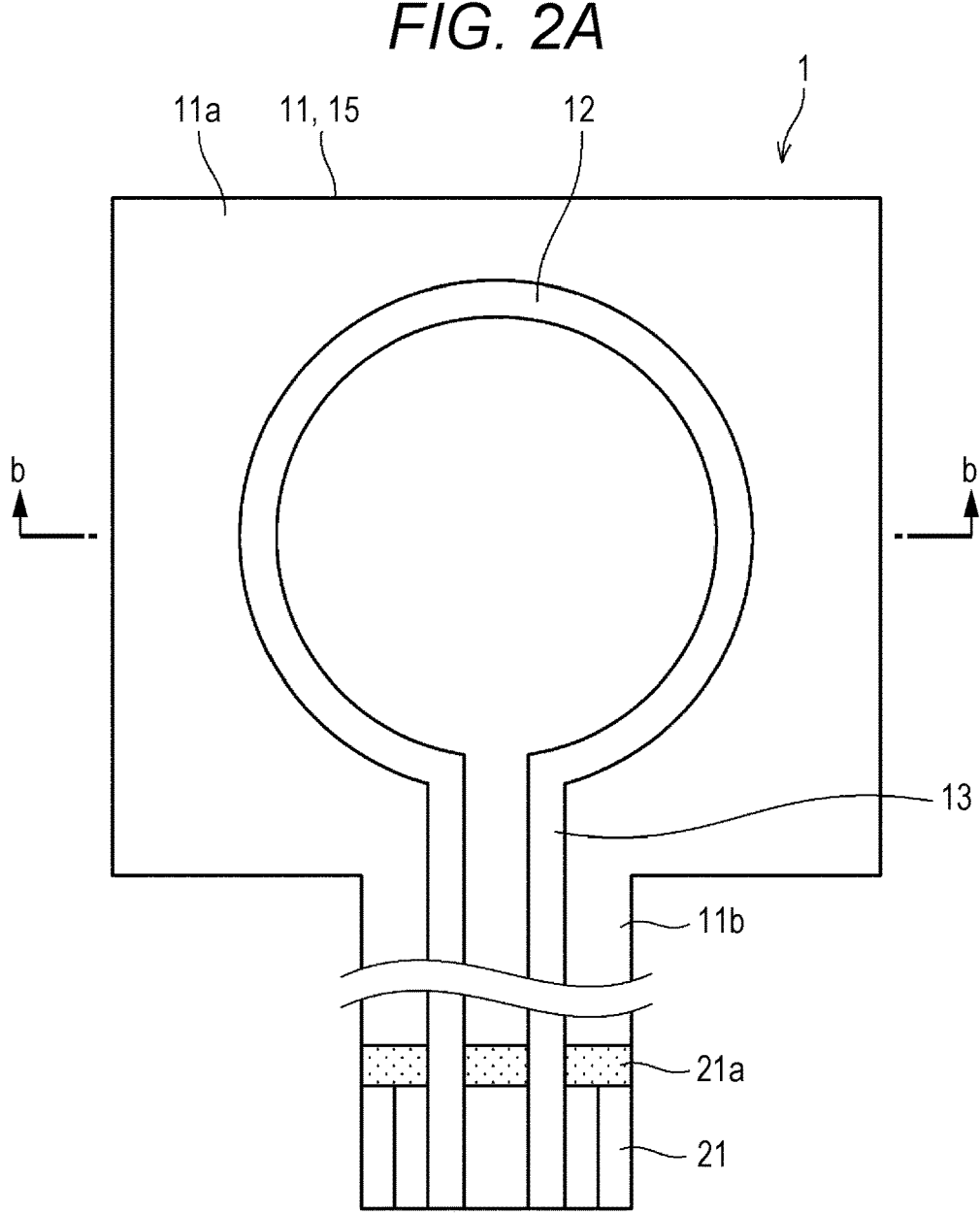
FIG. 2A is an enlarged view of the receiver illustrated in FIG. 1.
Figure 2B:
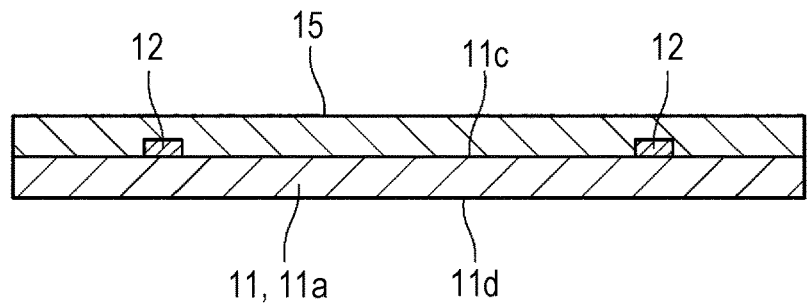
FIG. 2B is a sectional view of the receiver illustrated in FIG. 2A.

FIG. 1 is a view of a state when receivers 1 according to the first embodiment of the present disclosure are attached to a subject body (hereinafter referred to as a "living body") S. FIG. 2A illustrates the receiver 1 of FIG. 1 in close-up. FIG. 2A is a view for describing each configuration of the receiver 1. FIG. 2B is, from a direction indicated by arrows b, b, a sectional view of the receiver 1 illustrated in FIG. 2A.

As illustrated in FIG. 1, the multiple receivers 1 according to the first embodiment are attached to the living body S. Thus, the receivers 1 receive a signal transmitted from a transmitter 2 (FIG. 9) installed in the living body S. As illustrated in FIG. 2B, the receiver 1 includes a stretchable circuit board 11 having stretchability, and a receiving antenna 12 as a first antenna. The receiving antenna 12 is formed on a main surface 11c (a first main surface 11c) of the stretchable circuit board 11, and is configured to stretch in accordance with the stretchable circuit board 11. Further, the receiving antenna 12 is configured to receive the signal transmitted from the transmitter 2. According to the receiver 1 illustrated in FIGS. 1, 2A, and 2B, a stretchable cover 15 is formed on stretchable circuit board 11 and the receiving antenna 12. The stretchable cover 15 is a member configured to protect the receiving antenna 12 on the stretchable circuit board 11.

Stretching of the receiving antenna 12 in accordance with the stretchable circuit board 11 as described herein indicates that the receiving antenna 12 and the stretchable circuit board 11 both have stretchability, but equal stretchability is not required for the receiving antenna 12 and the stretchable circuit board 11. Note that for preventing rupturing of the receiving antenna 12 due to stretching of the stretchable circuit board 11, the receiving antenna 12 preferably has stretchability equal to or higher than that of the stretchable circuit board 11.

In the first embodiment, a conductive portion between the receiving antenna 12 and a terminal 21 will be described as a wiring line 13. The wiring line 13 according to the first embodiment is a stretchable wiring line having stretchability. The stretchable circuit board 11 includes a base portion 11a and a wiring substrate 11b. The receiving antenna 12 and a portion of the wiring line 13 are formed on the base portion 11a. Other portions of the wiring line 13 are formed on the wiring substrate 11b. The base portion 11a and the wiring substrate 11b have a rectangular shape as viewed from above. The terminal 21 is formed at one end portion of the wiring substrate 11b. In the first embodiment, the terminal 21 is inserted into a connector 22 illustrated in FIG. 1. Thus, the receiver 1 and a signal cable 20 illustrated in FIG. 1 are electrically connected to each other. Note that in the first embodiment, a non-stretchable portion 21a may be provided at the periphery of the terminal 21 to be inserted to/detached from the connector 22. The non-stretchable portion 21a has stretchability sufficiently lower than that of the stretchable circuit board 11. It can be said that the non-stretchable portion 21a is hard.

Each receiver 1 is attached to the living body S with a second main surface 11d closely contacting the living body S. The second main surface 11d is a back surface of the stretchable circuit board 11 opposite to the first main surface 11c. The stretchable circuit board 11 exhibits stickiness. Thus, the stretchable circuit board 11 can be attached in close contact with the living body S without an adhesive and the like. Note that the first embodiment is not limited to attachment of the receivers 1 to the living body S by using the stickiness of the stretchable circuit board 11. For example, in the first embodiment, it may be configured such that an adhesive layer is formed on the second main surface 11d. Further, in the first embodiment, it may be configured such that a clearance between the living body S and the receiver 1 is filled with jelly applied to the living body S.

Figure 8:
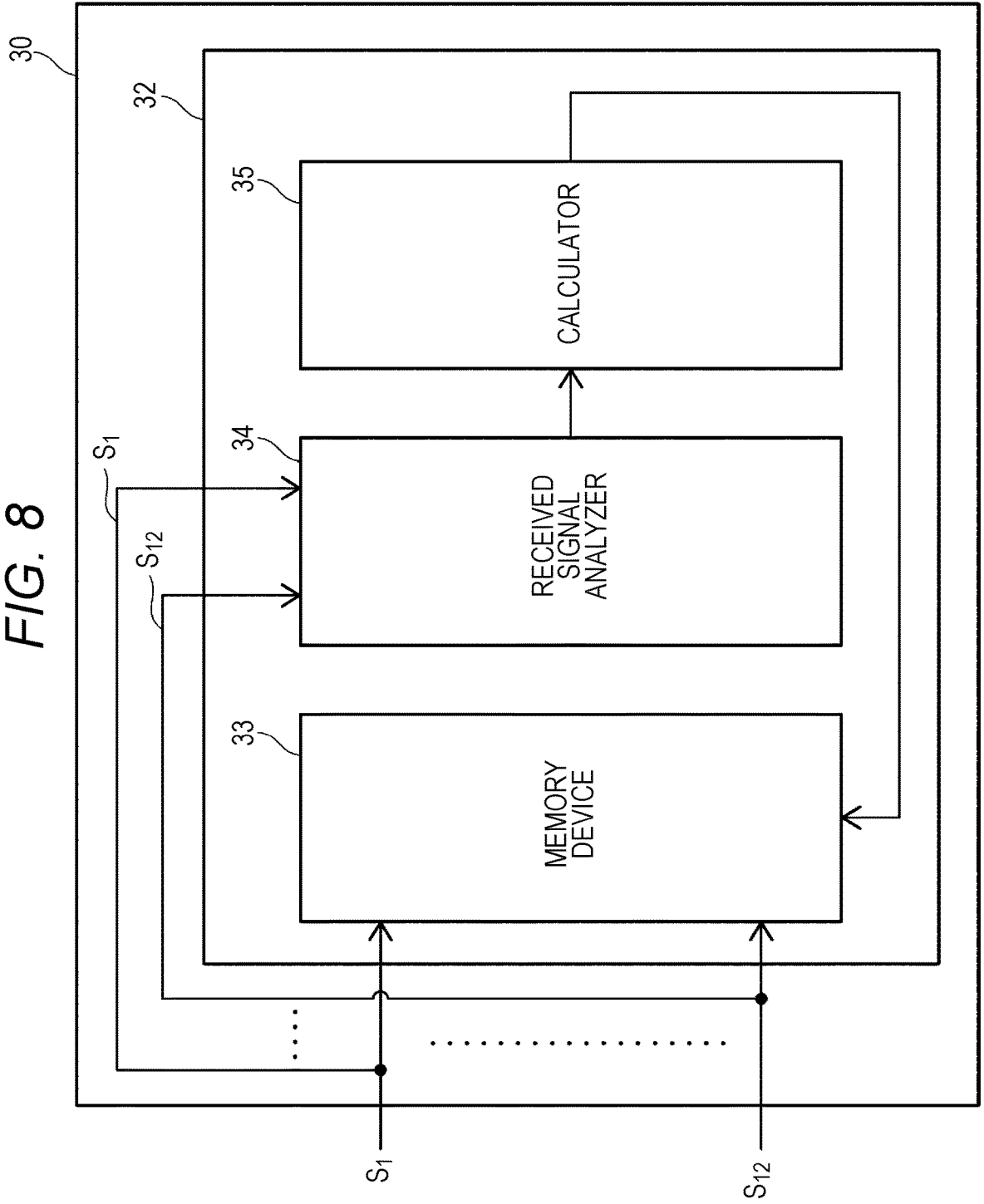
FIG. 8 is a functional block diagram for describing a transmitter position detector according to the third embodiment.

In the first embodiment, the signal received by the receiving antenna 12 is transmitted to a controller 30 via the wiring line 13, the terminal 21, and the signal cable 20. The controller 30 has a memory device 33 (FIG. 8). The signal received by each of the multiple receivers 1 is input to the memory device 33. The memory device 33 is configured to record and store such a received signal for each receiver 1.

The received signal stored in the memory device 33 may be recorded by outputting the received signal from the controller 30 to an external memory. Alternatively, the received signal stored in the memory device 33 may be recorded by transmitting the received signal to the outside via wireless communication of the controller 30 having a communication function. In the first embodiment, the controller 30 is fixed to a waist portion of the living body S (a subject) with a belt 31.

In the above-described configuration, the wiring substrate 11b may have stretchability, and may be attachable to the living body S. The wiring substrate 11b has optional length and shape. Thus, the wiring substrate 11b illustrated in FIG. 1 may have a greater length or a smaller length. According to the first embodiment, when the wiring substrate 11b has a smaller length, the wiring substrate 11b can be easily handled upon attach rent of the receiver 1. Conversely, according to the first embodiment, when the wiring substrate 11b has a greater length, the length of the signal cable 20 becomes smaller. This can reduce influence of the signal cable 20 on motion of the subject.

Hereinafter, the above-described configurations will be sequentially described.

(Stretchable Circuit Board)

The stretchable circuit board 11 is a sheet-shaped member stretchable in at least one of in-plane directions. The stretchable circuit board 11 is preferably stretchable in two of the in-plane directions. The stretchability of the stretchable circuit board 11 in the in-plane directions may exhibit isotropy or anisotropy. In a case where the stretchability of the stretchable circuit board 11 in the in-plane directions exhibits the anisotropy, the stretchability varies according to multiple directions in the plane of the stretchable circuit board 11. Preferably, a material contained in the stretchable circuit board 11 can include, but not limited to, an elastomer material such as nitrile rubber, latex rubber, urethane-based elastomer, or silicone-based elastomer. Specifically, even in a case where the stretchable circuit board 11 is attached to the skin of the human body with a urethane-based elastomer sheet for medical use, high safety can be obtained. The "sheet shape" described herein indicates a shape having a sufficiently-large area as compared to a thickness. The thickness or area of the sheet is not specifically defined. The stretchable circuit board 11 may be formed of a single layer including a single sheet-shaped member. Alternatively, the stretchable circuit board 11 may be formed of multiple layers including multiple sheet-shaped stretchable circuit boards.

The maximum stretch rate of the stretchable circuit board 11 is preferably equal to or higher than 10%, more preferably equal to or higher than 50%, much more preferably equal to or higher than 100%, and still much more preferably equal to or higher than 200%. The stretchable circuit board 11 containing the above-described material can exhibit, for example, a maximum stretch rate of equal to or higher than 300%. The maximum stretch rate of the stretchable circuit board 11 as described herein means the acceptable maximum value of the stretch rate when the stretchable circuit board 11 elastically deforms in one of the in-plane directions.

Note that in the present specification, the stretch rate means the percentage of stretching in one of the in-plane directions due to applied force with respect to dimensions when no external force is applied (dimensions at a stretch rate of 0%). For example, a stretch rate of 50% means a stretch rate when the dimensions increase to 1.5 times as large as the dimensions at a stretch rate of 0%. A stretch rate of 200% means a stretch rate when the dimensions increase to twice as large as the dimensions at a stretch rate of 0%.

The thickness of the stretchable circuit board 11 is not specifically limited. Note that the thickness of the stretchable circuit board 11 is preferably equal to or less than 100 μm, from a viewpoint that stretching or motion of a target (a target surface such as a living body surface) to which the stretchable circuit board 11 is attached is not inhibited. The thickness of the stretchable circuit board 11 is more preferably equal to or less than 25 μm, and much more preferably equal to or less than 10 μm.

As described above, according to the first embodiment, use of the thin sheet-shaped stretchable circuit board 11 having the stretchability does not inhibit motion of the subject to which the receivers 1 are attached. Thus, a load on the subject receiving treatment using the receivers 1 can be reduced. Moreover, the elastomer material exhibits air permeability. Thus, an uncomfortable feeling on the subject to which the receivers 1 are attached can be reduced.

Moreover, the non-stretchable portion 21a at the periphery of the terminal 21 at a tip end of the wiring substrate 11b can be, for example, formed in such a manner that a not-shown film base is attached onto the stretchable circuit board 11. The film base is a member exhibiting flexibility. The film base has a greater Young's modulus than that of the stretchable circuit board 11. According to the first embodiment, the film base is a member exhibiting lower stretchability than that of the stretchable circuit board 11 and being not substantially stretchable. A material of the film base is not specifically limited, but synthetic resin exhibiting low sliding properties, corrosion resistance, and high strength can be used. The synthetic resin includes, for example, polyethylene terephthalate (PET), polyethylene naphthalate (PEN), polyimide (PI), polyphenylene sulfide (PPS), and fluorine resin. In addition, a paper material exhibiting reasonable durability, such as cellulose nanofiber paper, may be used for the film base.

The thickness of the film base may fall within a range of equal to or greater than 10 μm and equal to or less than 200 μm, preferably a range of equal to or greater than 25 μm and equal to or less than 150 μm, and more preferably a range of equal to or greater than 50 μm and equal to or less than 100 μm.

Moreover, the thickness of the film base is preferably greater than that of the stretchable circuit board 11. With the thickness of the film base in the above-described range, in-plane stiffness of the non-stretchable portion 21a can be sufficiently enhanced, and the entire thickness of the receiver 1 can be reduced.

(Antenna, Stretchable Wiring Line)

The wiring line 13 and the receiving antenna 12 form a stretchable conductive pattern formed of a continuous layer. In the first embodiment, an annular portion, participating in signal transmission, of the conductive pattern will be described as the receiving antenna 12, and other portions of the conductive pattern will be described as the wiring line 13. In the first embodiment, the wiring line 13 and the receiving antenna 12 are formed on the outermost surface of the stretchable circuit board 11 formed of the single layer. However, the first embodiment is not limited to such a configuration. In a case where the stretchable circuit board 11 is formed of the multiple layers, the wiring line 13 and the receiving antenna 12 may be formed on at least one main surface of the multiple stretchable circuit boards included in the stretchable circuit board 11.

Moreover, in the first embodiment, the receiving antenna 12 is not limited to a loop antenna illustrated in FIGS. 1, 2A, and 2B. For example, the receiving antenna 12 may be a loop antenna obtained in such a manner that an antenna is wound multiple times. Alternatively, the receiving antenna 12 may be an antenna wound not in a circular ring shape but in a rectangular shape. As another alternative, the receiving antenna 12 may be, for example, a branched or comb-shaped antenna obtained by combination of straight antennas. That is, the receiving antenna 12 may be in any shape as long as the receiving antenna 12 has the function of receiving the signal.

Note that in the case of using the loop antenna obtained in such a manner that the antenna is wound multiple times, the antenna and the wiring line, in the first embodiment, may be connected by a connection wiring portion formed at another layer for connection between an inner portion of the antenna and the stretchable wiring line.

Figure 3:
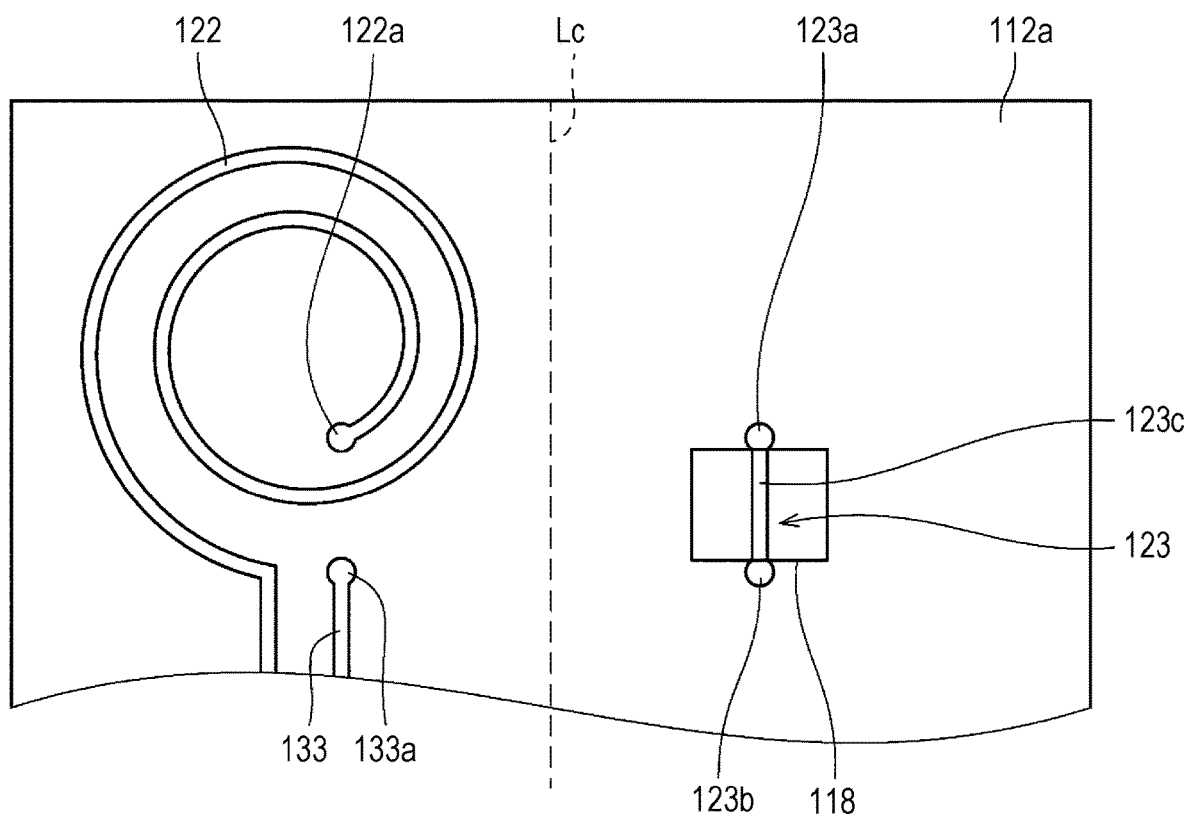
FIG. 3 is a view for describing an example of the method for connecting a receiving antenna and a wiring line according to the first embodiment.

FIG. 3 is a view for describing an example of the method for connecting a receiving antenna 122 and a wiring line 133 as described above. In FIG. 3, the receiving antenna 122, the wiring line 133, and a connection wiring portion 123 are formed on a base portion 112a of a stretchable circuit board 112. The receiving antenna 122 has a shape obtained in such a manner that an antenna is wound twice. An end portion of the receiving antenna 122 to be connected to the connection wiring portion 123 will be described as an end portion 122a. An end portion of the wiring line 133 to be connected to the end portion 122a will be described as an end portion 133a. Moreover, two end portions of the connection wiring portion 123 will be described as an end portion 123a and an end portion 123b, respectively. The entirety of a wiring portion 123c is covered with an insulating cover 118 formed on the wiring portion 123c between the end portion 123a and the end portion 123b.

For example, an elastomer material may be used for the insulating cover 118. A resin material common to that of the stretchable circuit board 11 may be used for the insulating cover 118. The insulating cover 118 may be a sheet containing the elastomer material. Alternatively, an elastomer-based potting material may be used as the insulating cover 118 to coat the wiring portion 123c.

The base portion 112a illustrated in FIG. 3 is valley-folded at a center line Lc, as a center, of FIG. 3 such that the end portion 122a and the end portion 123a overlap with each other and the end portion 133a and the end portion 123b overlap with each other. In this state, the end portion 122a and the end portion 123a contact each other, and the end portion 133a and the end portion 123b contact each other. The insulating cover 118 prevents or reduces contact of the wiring portion 123c with the receiving antenna 122. Thus, according to the connection method illustrated in FIG. 3, the receiving antenna 122 and the wiring line 133 can be electrically connected each other while short circuit is prevented or reduced. Note that the insulating cover 118 is preferably formed by potting, considering position alignment of the wiring portion 123c and the insulating cover 118 and reduction in the number of times of heating.

Note that the method using the configuration of connecting the receiving antenna 122 and the wiring line 133 by the connection wiring portion at another layer is not limited to the method in which the receiving antenna 122, the wiring line 133, and the connection wiring portion 123 formed on the same surface of the stretchable circuit board 112 overlap with each other. For example, a stretchable circuit board on which the receiving antenna 122 and the wiring line 133 are formed may overlap with another stretchable circuit board on which the insulating cover 118 and the connection wiring portion 123 are formed, so that the end portion 122a and the end portion 123a may be connected each other while the end portion 133a and the end portion 123a may be connected each other.

The receiving antenna 12 and the wiring line 13 contain a conductive material. Thus, the receiving antenna 12 and the wiring line 13 exhibit conductivity. A material with favorable conductivity can be selected as the conductive material. The material with favorable conductivity includes, for example, silver, gold, platinum, carbon, copper, aluminum, cobalt, nickel, and alloy thereof. The shape of the conductive material is not specifically limited, but may be a particle form such as granulated powder or powder. The particle form is not specifically limited, but may be a spherical shape, a needle shape, a flake shape, a nanowire shape or the like. A particle aspect ratio may fall within a range of equal to or greater than 1 and equal to or less than 100, and specifically a range of equal to or greater than 1 and equal to or less than 50, for example. The aspect ratio described herein means the ratio between the longest dimension and the shortest dimension of a three-dimensional body. When the aspect ratio of the particle contained in the receiving antenna 12 and the wiring line 13 falls within a range of equal to or greater than 5 and equal to or less than 20, a change in resistance when the stretchable circuit board 11 stretching in the in-plane directions deforms in a length direction can be reduced.

The receiving antenna 12 and the wiring line 13 preferably further contain a resin binder. That is, the receiving antenna 12 and the wiring line 13 according to the first embodiment are formed with the conductive material. This conductive material is obtained in such a manner that conductive particles are dispersed in a resin material while being mixed with the resin material. Since the receiving antenna 12 and the wiring line 13 contain the resin binder, rupturing of the receiving antenna 12 and the wiring line 13 due to stretching is reduced. The resin binder includes, but not limited to, a binder containing, as a main component, resin such as urethane or polyester, and a thermoplastic elastomer material such as silicone rubber, for example. Preferably, a resin binder with a low Young's modulus is selected such that the receiving antenna 12 and the wiring line 13 in the form of a coating have an elastic modulus equal to or less than that of the stretchable circuit board 11. A single type of elastomer material may be used. Alternatively, a mixture of multiple types of elastomer materials may be used.

The method for manufacturing the receiving antenna 12 and the wiring line 13 is not specifically limited. In the first embodiment, the receiving antenna 12 and the wiring line 13 are formed by a printing method. That is, the receiving antenna 12 and the wiring line 13 are printed patterns formed in such a manner that conductive paste having stretchability is printed and applied onto the first main surface 11c. The printing method is not specifically limited. The printing method may include, for example, a screen printing method, an inkjet printing method, a gravure printing method, and an offset printing method. Of these methods, screen printing is preferably used, considering fine resolution properties and film thickness stability. In the case of forming the receiving antenna 12 and the wiring line 13 by the printing method, conductive paste prepared to contain the above-described conductive particles, the above-described resin binder, and an organic solvent s preferably used. Stretchable conductive paste containing, as a main component, metal particles such as silver is used for the receiving antenna 12 and the wiring line 13, so that a stretch rate within a range of equal to or higher than 50% and equal to or lower than 70% can be realized, for example. Thus, a wiring line with excellent stretching properties can be formed.

The thickness and width dimensions of the receiving antenna 12 and the wiring line 13 can be determined based not only on resistivity under no load and a change in resistance upon stretching of the stretchable circuit board 11, but also on limitations of the thickness and width dimensions of the entirety of the stretchable circuit board 11. The width dimensions of the receiving antenna 12 and the wiring line 13 are preferably equal to or less than 1000 µm, more preferably equal to or less than 500 µm, and much more preferably equal to or less than 200 µm. The above-described width dimensions of the receiving antenna 12 and the wiring line 13 are based on the point of view that the receiving antenna 12 and the wiring line 13 follow a change in the dimensions upon stretching of the stretchable circuit board 11 while favorable stretchability is ensured. The thickness dimensions of the receiving antenna 12 and the wiring line 13 may be equal to or less than 25 µm, and preferably falls within a range of equal to or greater than 10 µm and equal to or less than 15 µm.

(Terminal)

As illustrated in FIGS. 2A and 2B, the receiver 1 includes the terminal 21 at one end portion of the wiring substrate 11b. The terminal 21 can be produced in such a manner that an abrasion-resistant conductive coating such as carbon paste is stacked. In the first embodiment, gold plating is applied to the terminal 21.

Note that a plating material for the terminal 21 of the first embodiment is not limited to gold. The plating material for the terminal 21 may include, for example, tin (Sn), nickel (Ni), zinc (Zn), and a solder material.

The terminal 21 is made of the carbon paste as described above, and therefore, has a high degree of hardness. It has been well-known that the terminal 21 easily breaks when the wiring line 13 containing soft metal is provided below the above-mentioned terminal 21. For this reason, in the first embodiment, the wiring line 13 overlaps with the terminal 21 to run on the terminal 21. This reduces a defect of the terminal 21.

(Stretchable Cover)

The stretchable cover 15 is a stretchable sheet-shaped cover configured to cover the first main surface 11c of the stretchable circuit board 11. The stretchable cover 15 according to the first embodiment is formed with such a size that the stretchable cover 15 reaches not only to the base portion 11a but also to the wiring substrate 11b. Note that the stretchable cover 15 has a not-shown opening on the terminal 21 such that the exposed terminal 21 is in conduction with the signal cable 20 in the connector 22.

The stretchable cover 15 preferably contains an insulating stretchable material. For example, an elastomer material can be used for the stretchable cover 15. Alternatively, a resin material common to that of the stretchable circuit board 11 may be used for the stretchable cover 15. According to the first embodiment, this can protect the wiring line 13 without damage to the stretchability of the stretchable circuit board 11 of the receiver 1. The stretchable cover 15 can be produced in such a manner that elastomer-based paste applied to the stretchable circuit board 11 and the non-stretchable portion 21a is dried. Alternatively, the stretchable cover 15 produced in a sheet shape in advance may be attached to the stretchable circuit board 11 and the non-stretchable portion 21a, or may be joined to the stretchable circuit board 11 and the non-stretchable portion 21a with an adhesive.

The thickness of the stretchable cover 15 is not specifically limited. From a viewpoint that the stretchability of the stretchable circuit board 11 is not inhibited, the thickness of the stretchable cover 15 is preferably equal to or less than 100 µm, more preferably equal to or less than 50 µm, and much more preferably equal to or less than 30 µm.

As described above, according to the receiver 1 of the first embodiment, the receiving antenna 12 having the stretchability is formed on the thin stretchable circuit board 11. Thus, after having been attached to the living body S, the receiver 1 stretches in accordance with motion of the living body S to exhibit a constant receiving state. Moreover, the receiver 1 including the stretchable circuit board 11 and the receiving antenna 12 stretches in accordance with motion of the living body S to have favorable adherence to the living body 5, the stretchable circuit board 11 and the receiving antenna 12 both having the stretchability. Thus, the receiver 1 can receive, with high sensitivity, the signal transmitted from the transmitter 2 in the living body S, and is less detachable from the living body S. According to the receiver 1 of the first embodiment as described above, the load on the subject receiving the treatment can be reduced, and high receiving sensitivity can be obtained.

Second Embodiment

Next, a receiver 3 according to the second embodiment of the present disclosure will be described. The receiver 3 according to the second embodiment has a transmission antenna 121 in addition to a receiving antenna 12. That is, the receiver 3 according to the second embodiment is different from that of the first embodiment in that a signal received from a transmitter 2 is wirelessly transmitted to the outside.

Figure 4A:
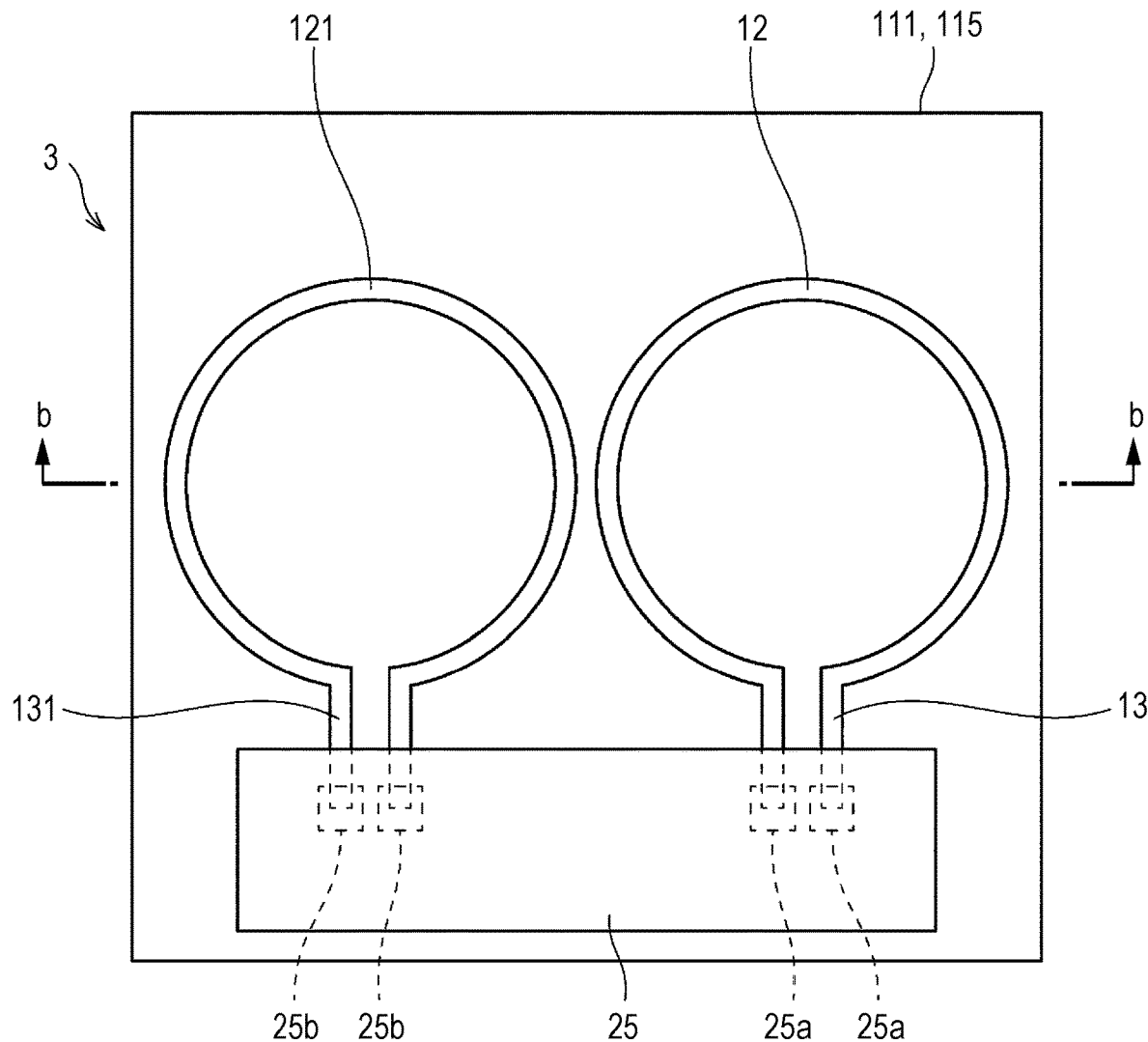
FIG. 4A is an upper view of a receiver according to a second embodiment.
Figure 4B:
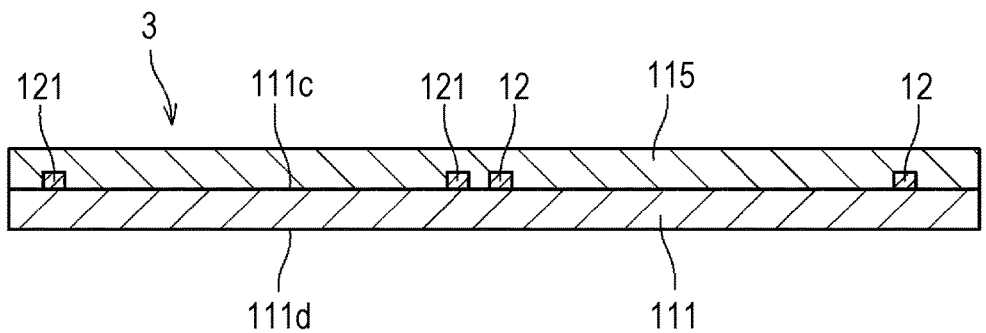
FIG. 4B is a sectional view of the receiver illustrated in FIG. 4A.

FIG. 4A is an upper view of the receiver 3 according to the second embodiment. FIG. 4B is a sectional view of the receiver 3 from the direction of arrows b, b of FIG. 4A. As illustrated in FIGS. 4A and 4B, the receiver 3 according to the second embodiment further includes, in addition to the configuration of the receiver 1 according to the first embodiment, the transmission antenna 121 configured to transfer the signal received by the receiving antenna 12.

The transmission antenna 121 is formed, with a material similar to that of the receiving antenna 12, on a main surface 111c (a first main surface 111c) of a stretchable circuit board 111 by a method similar to that of the receiving antenna 12. An opposite surface of the first main surface 111c is a main surface 111d (a second main surface 111d). The stretchable circuit board 111 is formed with a material similar to that of the stretchable circuit board 11. However, the stretchable circuit board 111 has no base portion or no wiring substrate. Further, the entirety of the stretchable circuit board 111 has a substantially square shape as viewed from above. On these points, the stretchable circuit board 111 is different from the stretchable circuit board 11 according to the first embodiment. The transmission antenna 121 is different from the receiving antenna 12 in an applied power range such as withstanding voltage. Thus, in the second embodiment, the receiving antenna 12 and the transmission antenna 121 are separately formed. Note that the receiving antenna 12 can be used in combination with the transmission antenna depending on design.

Moreover, the receiver 3 illustrated in FIGS. 4A and 4B includes a control circuit 25. The control circuit 25 is a compact integrated circuit (IC), such as a one-chip microcomputer, configured to control transfer (transmission) of the signal received by the receiving antenna 12. The control circuit 25 includes a pair of terminals 25a, 25a and another pair of terminals 25b, 25b. In the second embodiment, the terminals 25a are fixed while overlapping under a wiring line 13 of the receiving antenna 12. Moreover, the terminals 25b are fixed while overlapping under a wiring line 131 of the transmission antenna 121. Fixing of the wiring line 13 and each terminal 25a and fixing of the wiring line 131 and each terminal 25b are performed using a highly-flexible adhesive exhibiting conductivity, for example.

In the second embodiment, a stretchable cover 115 is also formed on the stretchable circuit board 111. Thus, the stretchable cover 115 protects the receiving antenna 12 and the transmission antenna 121.

The receiver 3 of the second embodiment as described above can wirelessly transfer the received signal. Thus, no signal cable 20 is necessary. According to the receiver 3, a subject can move without awareness of the signal cable 20 in treatment using the receiver 3. Thus, a load on the subject can be further reduced. Further, according to the receiver 3 of the second embodiment, the weight of the signal cable 20 is not applied on the stretchable circuit board 111. Thus, the receiver 3 is much less easily detached from a living body S.

Figure 5A:
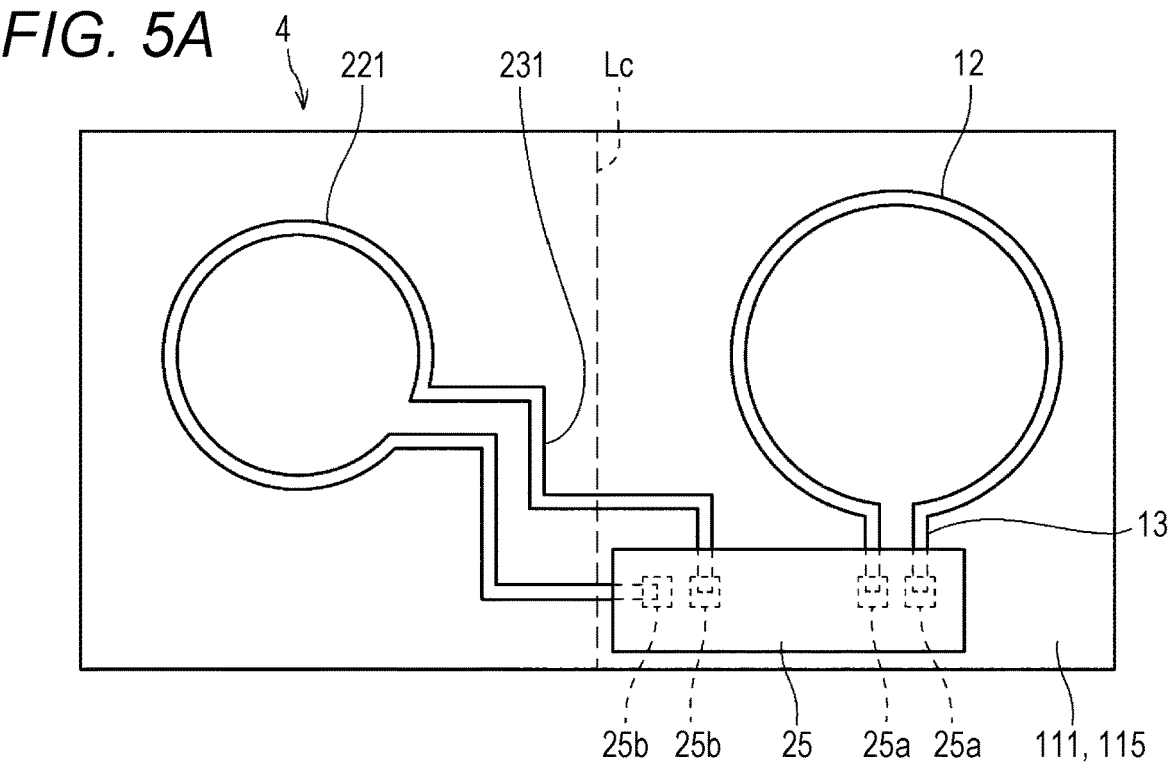
FIG. 5A is an upper view of the receiver according to the second embodiment in the course of manufacturing.
Figure 5B:
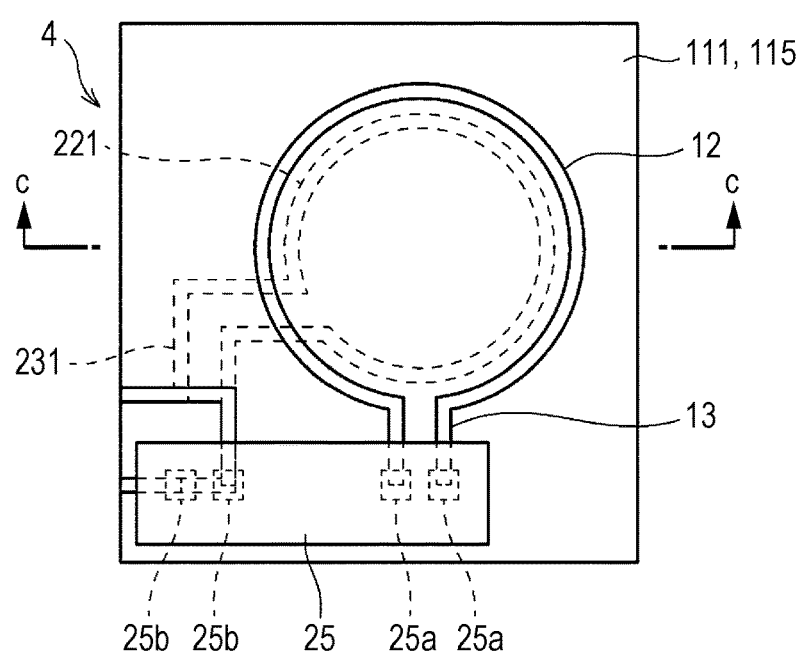
FIG. 5B is a view of the receiver according to the second embodiment from one main surface.
Figure 5C:
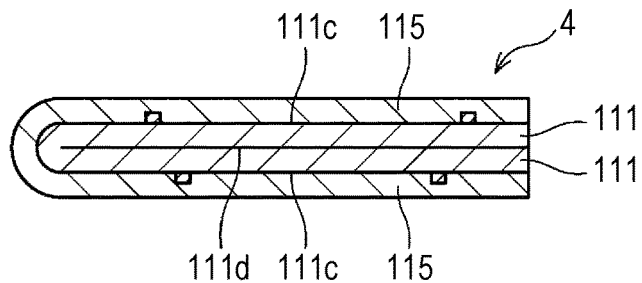
FIG. 5C is a sectional view of the receiver illustrated in FIG. 5B.

FIGS. 5A, 5B, and 5C are views for describing a receiver 4 as another configuration example of the second embodiment. The receiver 4 is obtained in such a manner that a configuration similar to that of the receiver 3 is formed on each surface of the folded stretchable circuit board 111.

FIG. 5A is an upper view of the receiver 4 according to the second embodiment in the course of manufacturing. FIG. 5B is a view of the receiver 4 from one main surface, FIG. 5C is a sectional view of the receiver 4 from the direction of arrows c, c of FIG. 5B. As illustrated in FIG. 5A, the receiving antenna 12, the wiring line 13, a transmission antenna 221, and a wiring line 231 are first formed on the stretchable circuit board 111 in the second embodiment. As illustrated in FIG. 5A, the receiver 4 is different from the receiver 3 of FIG. 4A in the shape of the wiring line 231 connecting the transmission antenna 221 and the terminals 25b. The wiring line 231 is formed such that the transmission antenna 221 and the terminals 25b are connected each other and that two wiring portions arranged in parallel do not cross each other.

The stretchable circuit board 111 illustrated in FIG. 5A is mountain-folded at a center line Lc, as a center, of the stretchable circuit board 111 such that the second main surface 111d is arranged inside. Since the stretchable circuit board 111 is folded, a side (a surface), of the stretchable circuit board 111, on which the transmission antenna. 221 and a portion of the wiring line 231 are formed is the back of a side (a surface) on which the receiving antenna 12 is formed, as illustrated in FIGS. 5B and 5C. That is, the surface of the stretchable circuit board 111 on which the transmission antenna 221 and the portion of the wiring line 231 are formed faces, in a thickness direction, the surface on which the receiving antenna 12 is formed.

As described above, in the receiver 4 of the second embodiment, the receiving antenna 12 and the transmission antenna 221 are arranged in a two-sided relationship. Alternatively, it can be said that the receiving antenna 12 and the transmission antenna 221 are arranged to face each other. The two-sided relationship described herein indicates the following arrangement. In such arrangement, the receiving antenna 12 or the transmission antenna 221 is formed on the first main surface 111c illustrated in FIG. 5C, and the receiving antenna 12 not formed on the first main surface 111c or the transmission antenna 221 not formed on the first main surface 111c is formed on a third main surface 111c. The third main surface 111c faces the first main surface 111c through the second main surface 111d in the thickness direction. It is not required that the positions of the receiving antenna 12 and the transmission antenna 221, when the receiving antenna 12 and the transmission antenna 221 are in the two-sided relationship, overlap with each other as viewed from one of the main surface 111c or the main surface 111d (as viewed in the thickness direction). The receiving antenna 12 and the transmission antenna 221 on the first main surface 111c or the third main surface 111c may be formed at locations (positions) in in-plane directions, the locations being different from each other as viewed from one of the main surface 111c or the main surface 111d (as viewed in the thickness direction). Moreover, in the second embodiment, the receiving antenna 12 and the transmission antenna 221 may partially or entirely overlap with each other as viewed from one of the main surface 111c or the main surface 111d (as viewed in the thickness direction). Further, part or the entirety of one of the receiving antenna 12 or the transmission antenna 221 may be arranged inside an outer edge of the other one of the receiving antenna 12 or the transmission antenna 221.

According to the receiver 4 in FIG. 5A, the stretchable cover 115 covers the main surface 111c of the stretchable circuit board 111. Thus, as illustrated in FIG. 5C, the front and back surfaces of the receiver 4 are covered with the stretchable cover 115. The stretchable cover 115 may be a single-layer sheet member formed on the main surface 111c. Alternatively, the stretchable cover 115 may have a multilayer structure including a layer formed on the main surface 111c before mounting of the control circuit 25 and a layer configured to cover the control circuit 25 after mounting of the control circuit 25. For example, a stretchable elastomer-based potting material can be used as the layer configured to cover the control circuit 25.

In the second embodiment, the receiver 4 may be attached to the living body S by using stickiness of the stretchable cover 115. Alternatively, in the second embodiment, the receiver 4 may be attached to the living body S by with adhesive layer provided on the stretchable cover 115 or jelly applied to the stretchable cover 115, for example.

According to the receiver 4, the received signal can be wirelessly transmitted as in the receiver 3, and an attachment area can be reduced as compared to that of the receiver 3. The receiver 4 with a smaller attachment area can further reduce subject's awareness of attachment of the receiver, and therefore, the load applied on the subject during the treatment can be further reduced.

Third Embodiment (Receiver)

Next, a receiver 5 according to the third embodiment of the present disclosure will be described. In the receiver 5 according to the third embodiment, multiple receiving antennas are formed on a single stretchable circuit board 11.

Figure 6:
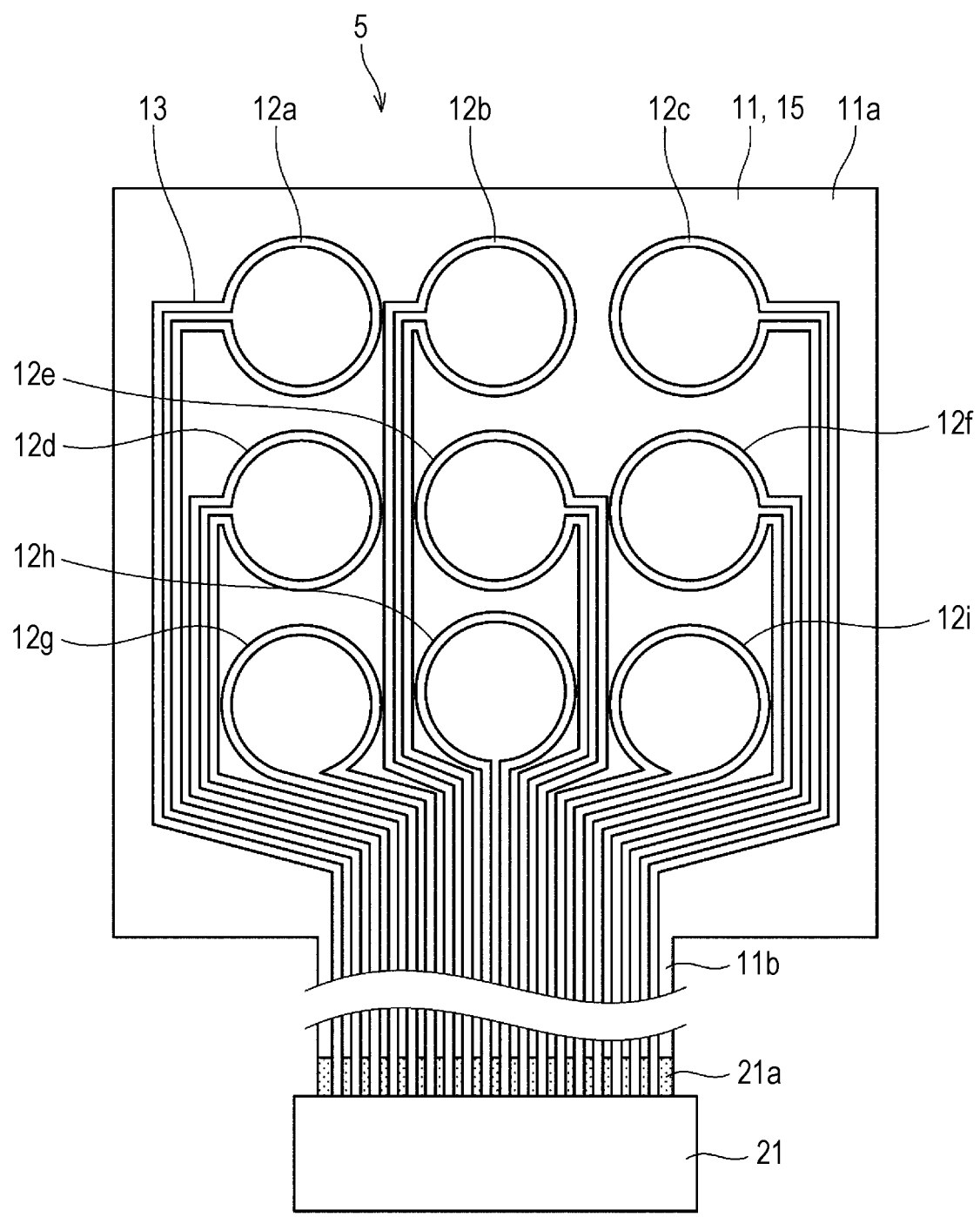
FIG. 6 is a view of a receiver according to a third embodiment as viewed from above.
Figure 7:
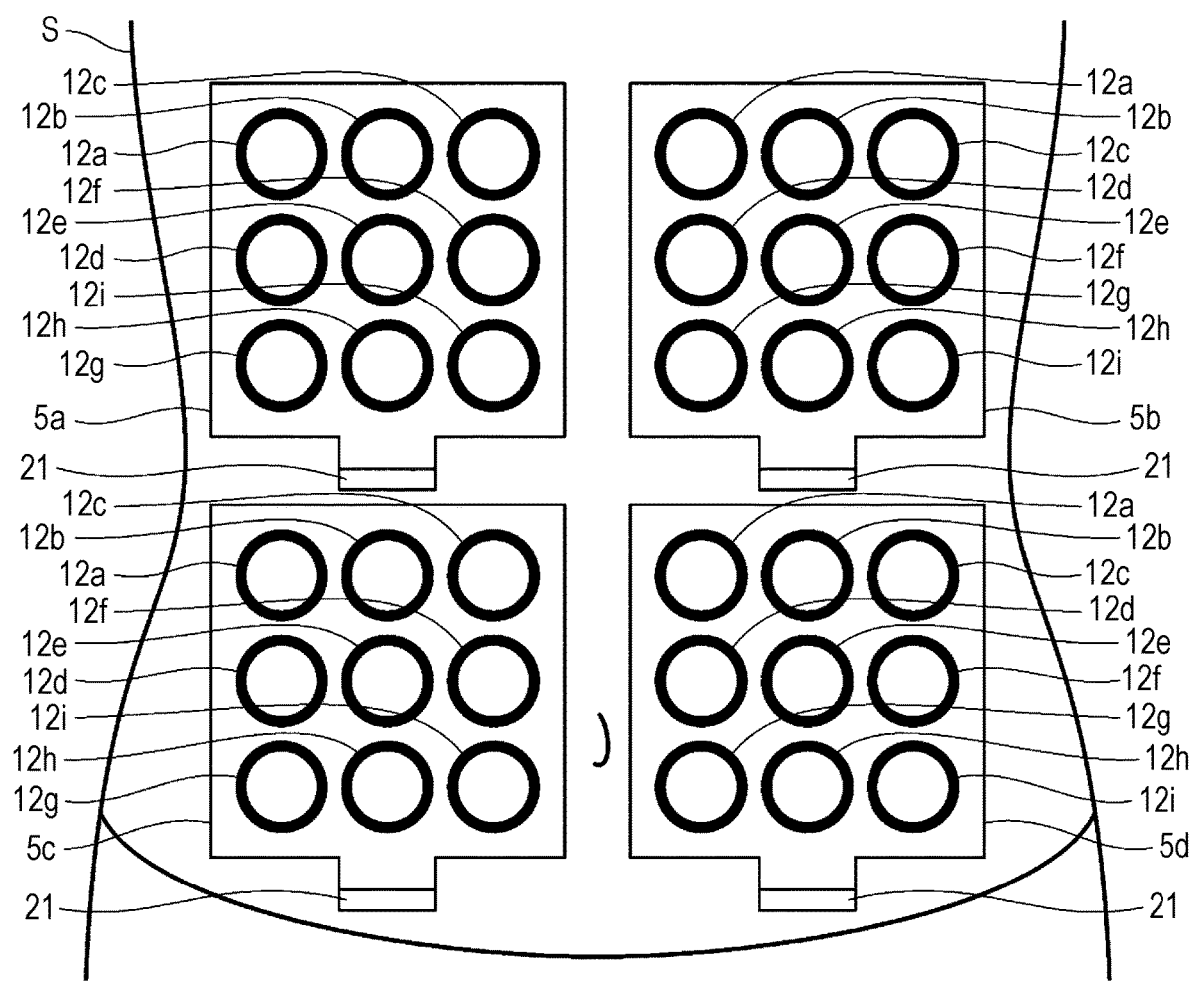
FIG. 7 is a view of a state when multiple receivers illustrated in FIG. 6 are attached to a living body.

FIGS. 6 and 7 are views for describing the receiver 5. FIG. 6 is the view of the receiver 5 as viewed from above. FIG. 7 illustrates a state when the multiple receivers 5 illustrated in FIG. 6 are attached to a living body S. In FIG. 7, the multiple receivers 5 are each illustrated as receivers 5a, 5b, 5c, 5d. In the third embodiment, nine receiving antennas are formed on the single stretchable circuit board 11 (FIG. 6) of each of the receivers 5a to 5d. These nine receiving antennas include receiving antennas 12a, 12b, 12c, 12d, 12e, 12f, 12g, 12h, 12i. When the receiving antennas 12a, 12b, 12c, 12d, 12e, 12f, 12g, 12h, 12i are not distinguished from one another, these receiving antennas will be hereinafter referred to as "multiple receiving antennas 12." A stretchable cover 15 is formed on the stretchable circuit board 11. The multiple receiving antennas 12 and wiring lines 13 are protected by the stretchable cover 15.

As in the first embodiment, the stretchable circuit board 11 according to the third embodiment includes a base portion 11a and a wiring substrate 11b. The wiring substrate 11b has an optional length. A terminal 21 is formed at one end portion of the wiring substrate 11b. All of the wiring lines 13 of the multiple receiving antennas 12 are connected to the terminal 21.

Note that in the third embodiment, it is configured such that the receiver 5 transmits a received signal to the outside via a wire. However, the third embodiment is not limited to such a configuration. In the third embodiment, it may be configured such that the receiver 5 having the multiple receiving antennas 12 wirelessly transmits the received signal as in the second embodiment. Alternatively, it may be configured such that the receiver 5 according to the third embodiment has a receiving antenna on one surface of the stretchable circuit board and a transmission antenna on the other surface of the stretchable circuit board.

In the receiver 5 of the third embodiment, the multiple receiving antennas 12 are arranged in a regular manner. The regular manner described herein indicates such arrangement that the same pattern such as a grid pattern or a staggered pattern is repeated. Moreover, in the third embodiment, e.g., an interval between the center points of at least some of the multiple receiving antennas 12 is constant.

According to the receiver 5 described above, the multiple receiving antennas 12 can be constantly or substantially constantly arranged in the regular manner on the living body S. Thus, according to the receiver 5, the multiple receiving antennas 12 can be more easily arranged at proper positions of the living body S as compared to, e.g., the receiving antenna 12 of the receiver 1.

Moreover, the receiver 5 has a larger attachment area than that of the receiver 1. Thus, detachment of the receiver 5 from the living body S is reduced as compared to that of the receiver 1. Consequently, according to the third embodiment, occurrence of antenna position displacement due to motion of a subject is reduced as compared to that of the first embodiment.

Further, according to the third embodiment, a large area of the living body S can be covered with the multiple receiving antennas 12 arranged in the regular manner, as illustrated in FIG. 7. According to the third embodiment described above, a transmitter in the living body can be seamlessly detected.

(Receiving System)

As described above, according to the third embodiment in which the multiple receiving antennas 12 are arranged in the regular manner, a receiving system configured to detect, with high accuracy, the position of the transmitter in the living body S can be built. The receiving system according to the third embodiment is a receiving system living body receiving the signal transmitted from the transmitter 2 installed in the living body S while the receiving system is attached to the living body S. The receiving system includes the receiver 5 according to the third embodiment and a transmitter position detector. The transmitter position detector is configured to detect, based on the position and received signal of each of the multiple receiving antennas of the receiver 5, the position of the transmitter 2 in the living body S, the transmitter 2 having transmitted the signal received by the receiver 5. In the third embodiment, the receiving system will be described with reference to an example where the received signal is an image signal obtained by capturing an image of the inside of the living body S.

FIG. 8 is a functional block diagram for describing the transmitter position detector 32 according to the third embodiment. The transmitter position detector 32 has a memory device 33, a received signal analyzer 34, and a calculator 35, The memory device 33 is configured to record and store the received signal as described above. The received signal analyzer 34 is configured to analyze the intensity of the received signal. The received signal analyzer 34 determines, based on the intensity of the received signal, a distance between the transmitter 2 transmitting/receiving the signal (received signal) and each receiving antenna 12. The calculator 35 is configured to determine, based on the distance determined by the received signal analyzer 34, the angle of the transmitter 2 with respect to the receiving antenna 12. The distance and the angle are information on the position of the transmitter 2 in the living body S. The position information detected by the transmitter position detector 32 is, together with the received signal as the image signal, stored in the memory device 33.

The transmitter position detector 32 having the above-described functions has a not-shown central processing unit (CPU), a not-shown working memory, and the like required for each type of processing.

Figure 9:
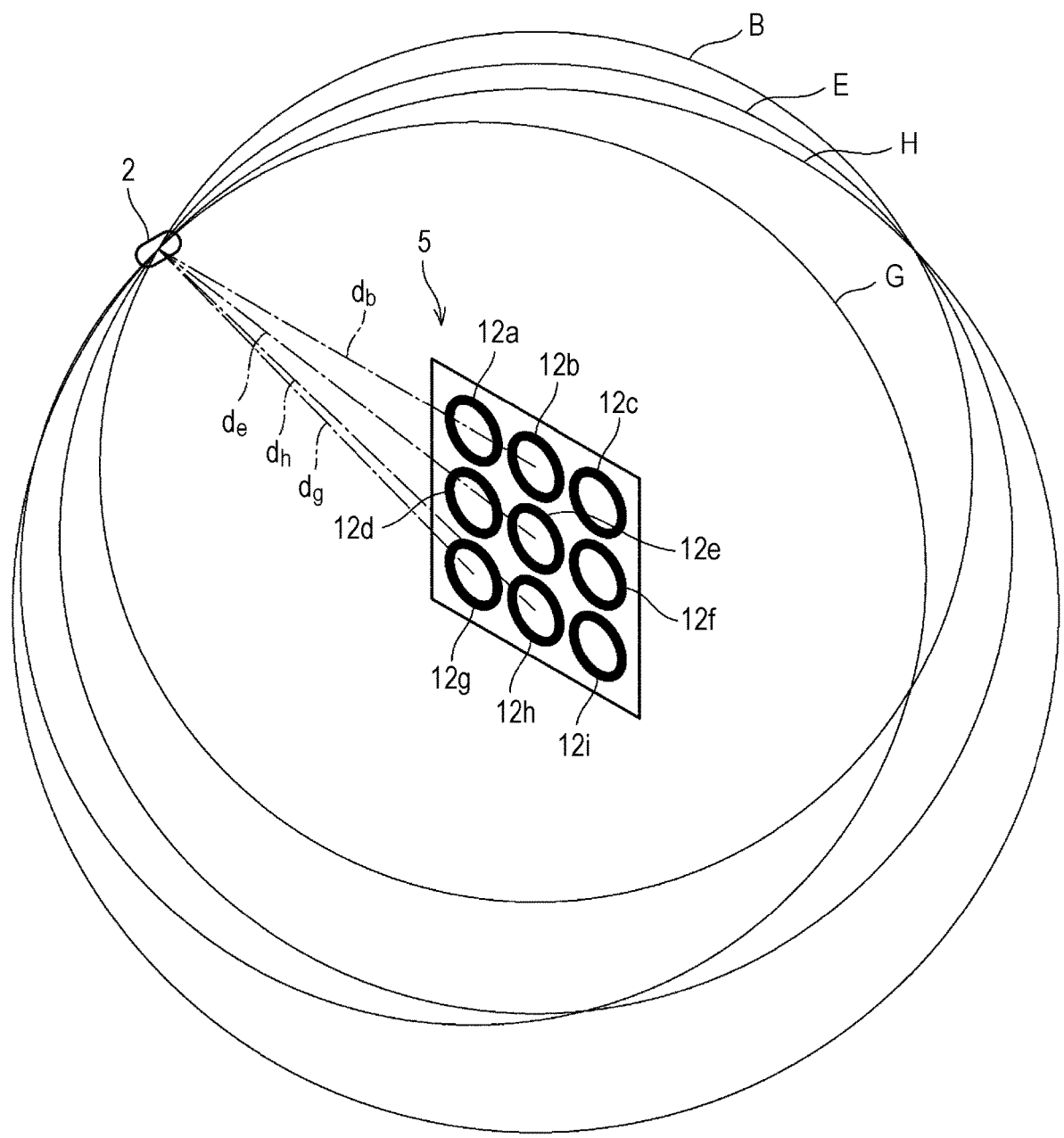
FIG. 9 is a view for describing an example of calculation processing executed by the transmitter position detector illustrated in FIG. 8.

FIG. 9 is a view for describing an example of calculation processing executed by the transmitter position detector 32. In FIG. 9, the receiver 5 and the transmitter 2 are illustrated. The receiver 5 has the multiple receiving antennas 12. The transmitter 2 configured to capture the image of the inside of the living body S to transmit the image signal is a capsule endoscope including a not-shown camera and a not-shown transmission part. Such a capsule endoscope is well-known, and therefore, further description thereof will not be made. According to the third embodiment, the position of the transmitter 2 is obtained based on the positions (the center points) of the multiple receiving antennas having received the signal transmitted from the single transmitter 2 and the intensity of the received signal for each receiving antenna.

Each of straight lines $d_b$, $d_e$, $d_g$, $d_h$ illustrated in FIG. 9 is a straight line connecting the position of the transmitter 2 (or the position of a predetermined portion of the transmitter 2) and the center point of the circular ring-shaped receiving antenna 12b, 12e, 12g, 12h. A straight line $L_\mu$ is a straight line connecting the center point of the receiving antenna 12a and the center point of the receiving antenna 12h. A straight line $L_\beta$ is a straight line connecting the center point of the receiving antenna 12b and the center point of the receiving antenna 12e.

Specifically, in, e.g., a case where the receiving antennas 12b, 12e, 12g, 12h receive significant signals, the received signal analyzer 34 converts the intensities of these signals into a distance between the receiving antenna 12b and the transmitter 2, a distance between the receiving antenna 12e and the transmitter 2, a distance between the receiving antenna 12g and the transmitter 2, and a distance between the receiving antenna 12h and the transmitter 2. In conversion processing, the received signal analyzer 34 determines, for example, as a short distance between the transmitter 2 and the receiving antenna when the intensity of the received signal is high. On the other hand, the received signal analyzer 34 determines as a long distance between the transmitter 2 and the receiving antenna when the intensity of the received signal is low. The signal intensity also changes depending on a tissue of the living body S, such as bones, fat, and muscles. Note that in the third embodiment, the multiple receiving antennas are arranged on the single stretchable circuit board 11 while being relatively close to each other. Thus, in the third embodiment, it is assumed that the multiple receiving antennas on the single stretchable circuit board 11 receive the signals transmitted through the substantially same body tissue.

In the third embodiment, the lengths of the straight lines $d_b$, $d_e$, $d_g$, $d_h$ are determined by the above-described processing. As illustrated in FIG. 9, it is assumed that the transmitter 2 is positioned at an intersection among a surface of a sphere B, a surface of a sphere E, a surface of a sphere G, and a surface of a sphere H. The radiuses of the spheres B, E, G, H are each the straight lines $d_b$, $d_e$, $d_g$, $d_h$.

Figure 10:
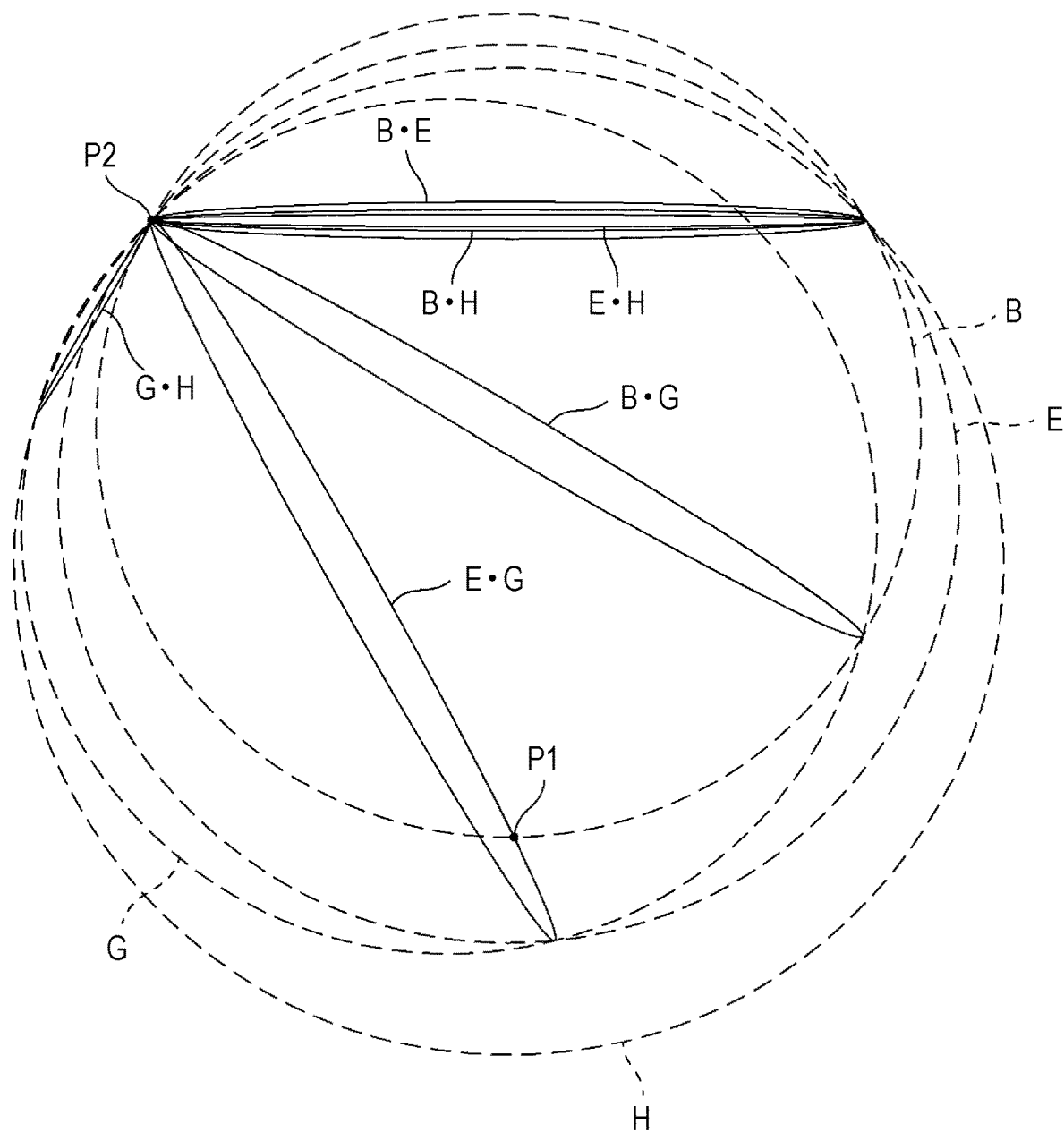
FIG. 10 is a view in which surfaces of spheres illustrated in FIG. 9 are indicated by dashed lines and an intersecting circle of two spheres is indicated by a solid line.

In FIG. 10, the surfaces of the spheres B, E, G, H illustrated in FIG. 9 are indicated by dashed lines, and a line (hereinafter referred to as an "intersecting circle") formed by a continuous intersection between the surfaces of two spheres is indicated by a solid line. In FIG. 10, the intersecting circle of the surfaces of the spheres B, E is indicated by "B•E," for example. Moreover, the intersecting circle of the surfaces of the spheres B, G is indicated by "B•G," the intersecting circle of the surfaces of the spheres B, H is indicated by "B•H," the intersecting circle of the surfaces of the spheres E, G is indicated by "E•G," the intersecting circle of the surfaces of the spheres E, H is indicated by "E•H," and the intersecting circle of the surfaces of the spheres G, H is indicated by "G•H" The transmitter 2 is at any position on the intersecting circle. Thus, the position of the transmitter 2 cannot be identified from only two received signals of the receiving antennas.

Considering the intersection between the intersecting circle E•G and the surface of the sphere B, the intersecting circle E•G and the surface of the sphere B intersect each other at points P1, P2 in FIG. 10. That is, according to the third embodiment, the position of the transmitter 2 can be narrowed down to two points based on the received signals of each of three receiving antennas. Focusing on a relationship among the point P1, the point P2, and the sphere H, it is recognized that the point P2 is on the surface of the sphere H. That is, it is recognized that the transmitter 2 is at the position of the point P2. From above, the calculator 35 according to the third embodiment uses the received signals of four receiving antennas, thereby determining the distance between each of four receiving antennas and the transmitter 2. Then, the intersections of the surfaces of the four spheres are obtained by calculation processing, the spheres having the center position of each receiving antenna as the centers thereof and the radiuses thereof being the above-described distances, and in this manner, the position of the transmitter 2 is identified.

As described above, according to the third embodiment, the position of the transmitter 2 in the living body S can be three-dimensionally identified. Enhancement of the accuracy of position determination for the multiple receiving antennas 12 can improve the accuracy of the identified position of the transmitter 2. In the third embodiment described above, the receiver 5 configured so that the positions of the multiple receiving antennas 12 can be determined with high accuracy is effective for three-dimensionally detecting the position of the transmitter 2.

Moreover, according to the third embodiment, the position of the transmitter 2 is simultaneously detected by using more receiving antennas, so that the accuracy of position detection for the transmitter 2 can be further enhanced.

The position of the transmitter 2 detected by the transmitter position detector 32 may be, in the memory device 33, saved corresponding to an image indicated by the received signal used for position detection, for example. In this manner, the position of the transmitter 2 and the image of the inside of the living body S captured at such a position are, in the third embodiment, saved in association with each other. Thus, according to the third embodiment, not only the state of the inside of the living body S can be visually checked, but also the position of the tissue in such a state can be three-dimensionally identified.

The above-described embodiments and examples include the following technical ideas.

A receiver <1> attached to a living body to receive a signal transmitted from a transmitter installed in the living body includes a stretchable circuit board having stretchability, and a first antenna formed on a main surface of the stretchable circuit board, configured to stretch in accordance with the stretchable circuit board, and configured to receive the signal transmitted from the transmitter.

A receiver <2> is the receiver <1> further including a second antenna used for transfer of the signal received by the first antenna.

A receiver <3> is the receiver <2> in which the first antenna and the second antenna are arranged in a two-sided relationship.

A receiver <4> is any one of the receivers <1> to <3> in which the first antenna includes multiple first antennas formed on the single stretchable circuit board.

A receiver <5> is the receiver <4> in which the multiple first antennas are arranged in a regular manner.

A receiving system <6> is a receiving system attached to a living body to receive a signal transmitted from a transmitter installed in the living body. The receiving system includes the receiver <4> or <5> and a transmitter position detector configured to detect, based on the position and received signal of each of the multiple first antennas of the receiver, the position of the transmitter in the living body, the transmitter having transmitted the signal received by the receiver.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A receiver comprising:
   a stretchable circuit board having stretchability;
   a first antenna formed on a main surface of the stretchable circuit board, the first antenna being configured to stretch in accordance with the stretchable circuit board and configured to receive a signal transmitted from a transmitter installed in a living body, the first antenna including a first wiring portion arranged at a first location on the stretchable circuit board;
   a second wiring portion arranged at a second location on the stretchable circuit board, the first location and the second location overlapping when viewed in a thickness direction of the stretchable circuit board while the stretchable circuit board is folded along an axis; and
   an electrical insulator that is located between at least part of the first wiring portion and at least part of the second wiring portion when viewed in a direction along the axis while the stretchable circuit board is folded along the axis.

2. The receiver according to claim 1, further comprising:
a second antenna configured to transfer the signal received by the first antenna.

3. The receiver according to claim 2, wherein
the first antenna and the second antenna are arranged on the main surface of the stretchable circuit board to be on opposite sides of a second main surface of the stretchable circuit board while the stretchable circuit board is folded along an axis.

4. The receiver according to claim 1, wherein
the first antenna includes multiple first antennas formed on the single stretchable circuit board.

5. The receiver according to claim 4, wherein
the multiple first antennas are arranged in a repeating pattern.

6. A receiving system comprising:
a receiver including,
   a stretchable circuit board having stretchability; and
   a first antenna formed on a main surface of the stretchable circuit board, the first antenna being configured to stretch in accordance with the stretchable circuit board and configured to receive a signal transmitted from a transmitter installed in a living body, the first antenna including multiple first antennas formed on the single stretchable circuit board; and
a transmitter position detector configured to detect, based on a position and a received signal of each of the multiple first antennas of the receiver, a position of the transmitter in the living body, the transmitter having transmitted the signal received by the receiver.

7. The receiver according to claim 2, wherein
the first antenna includes multiple first antennas formed on the single stretchable circuit board.

8. The receiver according to claim 3, wherein
the first antenna includes multiple first antennas formed on the single stretchable circuit board.

9. The receiver according to claim 7, wherein
the multiple first antennas are arranged in a repeating pattern.

10. The receiver according to claim 8, wherein
the multiple first antennas are arranged in a repeating pattern.

11. A receiving system comprising:
the receiver according to claim 5; and
a transmitter position detector configured to detect, based on a position and a received signal of each of the multiple first antennas of the receiver, a position of the transmitter in the living body, the transmitter having transmitted the signal received by the receiver.

12. A receiving system comprising:
the receiver according to claim 7; and
a transmitter position detector configured to detect, based on a position and a received signal of each of the multiple first antennas of the receiver, a position of the transmitter in the living body, the transmitter having transmitted the signal received by the receiver.

13. A receiving system comprising:
the receiver according to claim 8; and
a transmitter position detector configured to detect, based on a position and a received signal of each of the multiple first antennas of the receiver, a position of the transmitter in the living body, the transmitter having transmitted the signal received by the receiver.

14. A receiving system comprising:
the receiver according to claim 9; and
a transmitter position detector configured to detect, based on a position and a received signal of each of the multiple first antennas of the receiver, a position of the transmitter in the living body, the transmitter having transmitted the signal received by the receiver.

15. A receiving system comprising:
the receiver according to claim 10; and
a transmitter position detector configured to detect, based on a position and a received signal of each of the multiple first antennas of the receiver, a position of the transmitter in the living body, the transmitter having transmitted the signal received by the receiver.

16. The receiver of claim 1, wherein,
the electrical insulator further comprises an insulating cover that covers the second location when viewed in the thickness direction of the stretchable circuit board while the stretchable circuit board is flattened along the axis, and
the insulating cover prevents contact between at least part of the first wiring portion and at least part of the second wiring portion in the thickness direction of the stretchable circuit board while the stretchable circuit board is valley folded along the axis.

17. The receiver of claim 1, wherein,
the electrical insulator further comprises a portion of the stretchable circuit board under the first wiring portion when viewed in the thickness direction of the stretchable circuit board, and
the portion of the stretchable circuit board under the first wiring portion prevents contact between at least part of the first wiring portion and at least part of the second wiring portion in the thickness direction of the stretchable circuit board while the stretchable circuit board is mountain folded along the axis.

* * * * *